(12) United States Patent
Heldmann et al.

(10) Patent No.: US 7,081,537 B2
(45) Date of Patent: Jul. 25, 2006

(54) PROCESS FOR THE ELECTROPHILIC SUBSTITUTION OF THIAZOLIDINES OR OXAZOLIDINES

(75) Inventors: Dieter Heldmann, München (DE); Jürgen Stohrer, Pullach (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 219 days.

(21) Appl. No.: 10/785,627

(22) Filed: Feb. 24, 2004

(65) Prior Publication Data

US 2004/0171840 A1     Sep. 2, 2004

(30) Foreign Application Priority Data

Feb. 27, 2003   (DE) ............................... 103 08 580

(51) Int. Cl.
C07D 277/06   (2006.01)
C07D 263/06   (2006.01)

(52) U.S. Cl. ...................................... 548/201; 548/215
(58) Field of Classification Search .............. 548/201, 548/215
See application file for complete search history.

(56) References Cited

U.S. PATENT DOCUMENTS

2003/0088105 A1   5/2003   Krich et al. ................ 548/201

FOREIGN PATENT DOCUMENTS

WO   WO 01/72702   10/2001
WO   WO 01/72703   10/2001

OTHER PUBLICATIONS

Seebach et al., Helvetica Chimica Acta, 1987, vol. 70, No. 4, pp. 1194-1216.
Moloney et al., Tetrahedron: Asymmetry, Elsevier Science Ltd., 1994, vol. 5, No. 8, pp. 1477-1478.
Moloney et al., Journal of the Chemical Society, Perkin Transactions 1, 1996, pp. 227-228.
Seebach et al., Tetrahedron Letters, 1984, vol. 25, No. 24, pp. 2545-2548.
Seebach et al., Helvetica Chimica Acta, 1987, vol. 70, pp. 1194-1216.
G. Pattenden et al., Tetrahedron Letters, 1993, vol. 49, No. 10, pp. 2131-2138.
G. Mulqueen et al., Tetrahedron, 1993, vol. 49, No. 24, pp. 5359-5364.
Seebach et al., Angew. Chem. 1988, 100, pp. 1685-1715.
Protecting Groups, P.J. Kocienski, Thieme Verlag, 1994, pp. 185-243.
Protecting Groups, P.J. Kocienski, Thieme Verlag, 1994, pp. 118-154.

*Primary Examiner*—Kamal A. Saeed
*Assistant Examiner*—Jason M. Nolan
(74) *Attorney, Agent, or Firm*—Collard & Roe, P.C.

(57) ABSTRACT

A process for preparing α-functionalized thiazolidines or oxazolidines, each of which are oxycarbonyl-functionalized in the 4-position, by adding a base to a reaction mixture comprising an oxycarbonyl-functionalized thiazolidine or oxazolidine and an electrophile at a temperature of greater than −40° C.

16 Claims, No Drawings

PROCESS FOR THE ELECTROPHILIC SUBSTITUTION OF THIAZOLIDINES OR OXAZOLIDINES

BACKGROUND OF THE INVENTION

1. Field of the Invention

The invention relates to a process for electrophilically substituting thiazolidines or oxazolidines. The process is especially suitable for diastereoselectively electrophilically substituting thiazolidines or oxazolidines.

2. The Prior Art

The electrophilic α-functionalization of thiazolidines or oxazolidines, each of which are oxycarbonyl-functionalized in the 4-position, is a known synthetic strategy for α-functionalizing amino acids. The process is especially suitable for preparing α-functionalized, enantiomerically pure, unnatural amino acids.

It is known that compounds of the general formula (1) can be obtained, for example, by reacting the esters or the free acids ($R^1$ may quite generally be hydrogen, a silyl or an organic radical) of the amino acids cysteine and serine (X is S or O) in the course of a condensation reaction with an aldehyde $R^2$—CHO ($R^2$ is an organic radical) and subsequent introduction of an amino protecting group P. The thiazolidine or oxazolidine derivatives prepared in this way may subsequently be further modified by introducing an electrophilic radical E into the 4-position by deprotonation and subsequent electrophilic substitution to obtain compounds of the general formula (2):

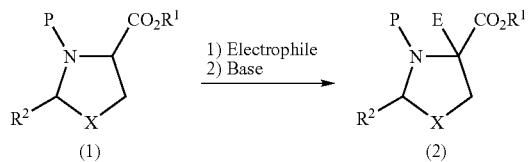

When the natural amino acids L-cysteine and L-serine or their unnatural D forms and a suitable $R^2$ radical are selected to prepare the thiazolidine or oxazolidine derivatives of the general formula (1), the electrophilic substitution on the possible enantiomers or diastereomers resulting from two chiral centers in the 2- and in the 4-position of the heterocycle proceeds diastereoselectively in the 4-position and the compounds of the general formula (2) are obtained in the form of their pure optical isomers. This is illustrated by way of example in the form of the optical isomers of the general formulae (1a) and (2a) which are obtainable from the L forms of the amino acids cysteine and serine:

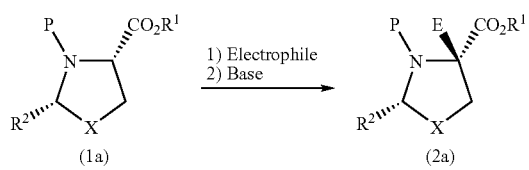

Final hydrolytic cleavage of compounds of the general formula (2) leads to α-substituted amino acid derivatives or their amine hydro salts of the general formula (4):

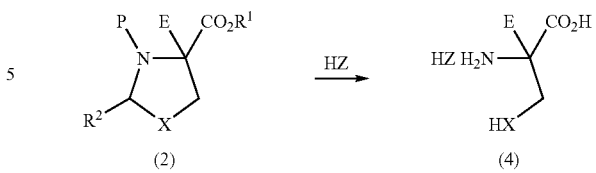

Depending on the $R^2$ radical and prior diastereoselective reaction control, enantiomerically pure α-substituted cysteine or serine derivatives (4a) result, as illustrated here by way of example for one possible optical configuration.

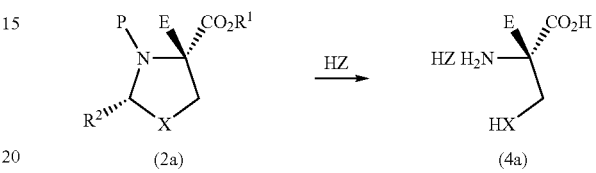

As unnatural α-substituted amino acids, the enantiomerically pure or impure amino acid derivatives obtained by this general principle are valuable intermediates for the further conversion to various pharmaceuticals.

In the prior art, a series of processes have been described for the electrophilic substitution in the 4-position of compounds of the general formula (1), especially for the special case of methylation in the 4-position of the thiazolidine (X=S) or oxazolidine (X=O) which derive from cysteine methyl ester and serine methyl ester respectively, in which $R^2$ is a tert-butyl radical and P is a formyl group.

For instance, D. Seebach et al. (Tetrahedron Lett. 1984, 25, 2545–2548, Helv. Chim. Acta 1987, 70, 1194–1216) describe the preparation of enantiomerically pure L-2-methylserine by alkylating the corresponding oxazolidine with methyl iodide. In this method, a solution of lithium diisopropylamide in THF/hexane with optional addition of hexamethylphosphoramide (HMPA) is initially charged at −78° C., and to this solution are added the oxazolidine and, after a further 10 min at −78° C., the electrophile methyl iodide. Within 12 h, the mixture is warmed to 0° C. and then worked up.

The methylation of corresponding thiazolidines with methyl iodide has been described in the preparation of enantiomerically pure L-/D-2-methylcysteine hydrochloride by G. Pattenden et al. (Tetrahedron 1993, 49(10), 2131–2138) and G. Mulqueen et al. (Tetrahedron 1993, 49(24), 5359–5364). Similar processes are also described in WO 01/72702 and WO 01/72703. In one possible variant, the thiazolidine is dissolved at −78° C. in THF with 1,3-dimethyltetrahydro-2(1H)-pyrimidone (DMPU) as a cosolvent, lithium hexamethyldisilazide in THF is added, the electrophile methyl iodide is added at −78° C. and finally, after 4 h at −78° C., the mixture was warmed to room temperature and worked up.

In a further variant, LiCl is dissolved homogeneously in 1,2-dimethoxyethane and THF, the thiazolidine is added at −65° C. dissolved in THF, the electrophile methyl iodide is added, and the base lithium hexamethyldisilazide is subsequently added at −65° C. and reacted at −65° C. for 10 h, and the mixture is finally warmed to room temperature and worked up.

In a third variant, DMPU is added at −78° C. to a solution of lithium diisopropylamide in hexane/THF, cooled to −90° C., then the thiazolidine is added in THF, the electrophile methyl iodide is added at −90° C. and, after 2 h at −90° C., warmed to room temperature and worked up.

In these processes, maximum yields of pure product of 46–63% are obtained after chromatographic workup.

The prior art processes described for the laboratory scale have a series of disadvantages, especially for industrial scale reaction. For instance, the use of extremely low temperatures cannot be realized on the industrial scale or is associated with disproportionately high costs.

The low reaction temperatures subsequently lead to uneconomically long reaction times and to a low solubility of the reactants in the solvents used, which in turn requires the use of large amounts of solvent and ultimately has a negative effect on the space-time yield.

The addition of cosolvents or lithium salts, which are used only as additives and consequently do not occur in the product, causes additional costs, and the auxiliaries also have to be removed again completely from the product in additional workup steps, in order to satisfy the high purity requirements on pharmaceutical intermediates.

The prior art electrophilic substitution processes of compounds of the general formula (1) for the preparation of unnatural, α-substituted amino acids of the general formula (4) consequently have a series of disadvantages which make scale-up from the laboratory scale to the industrial scale reaction uneconomic and inefficient.

SUMMARY OF THE INVENTION

It is therefore an object of the invention to provide a process for preparing compounds of the general formula (2) which is economically viable and can be carried out on the industrial scale.

This object is achieved by the development of a process for electrophilically substituting compounds of the general formula (1), which can be carried out at distinctly higher temperatures and dispenses with the use of additional auxiliaries.

It has been found that, surprisingly, the selection of suitable reaction conditions, in particular the reaction temperature, allows the auxiliaries which are disclosed by the literature and have a positive effect on the progress of the reaction, in particular lithium salt additives which lead to the formation of intermediate lithium enolates, as described by D. Seebach et al. (Angew. Chem. 1988, 100, 1685–1715), to be dispensed with.

The present invention provides a process for preparing compounds of the general formula (2)

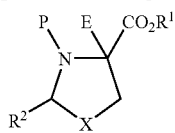

(2)

where

X is S or O, and $R^1$ is selected from the group comprising hydrogen, metals of the first or second main group, linear or branched $C_1$–$C_{12}$-alkyl, $C_6$–$C_{15}$-aryl or $C_7$–$C_{21}$-aralkyl radicals, dialkylsilyl, trialkylsilyl, dialkylarylsilyl, diarylalkylsilyl, triarylsilyl radicals, and the organic radicals of the silyl radicals are in turn selected from $C_1$–$C_{12}$-alkyl and $C_6$–$C_{15}$-aryl radicals, and $R^2$ is selected from the group comprising linear or branched $C_1$–$C_{12}$-alkyl, $C_6$–$C_{15}$-aryl and $C_7$–$C_{21}$-aralkyl radicals and P is an amino protecting group, and E is a radical selected from the group comprising optionally halogen, cyano, nitro or ester group-substituted, linear or branched $C_1$–$C_{12}$-alkyl, $C_3$–$C_{10}$-alkenyl, $C_6$–$C_{15}$-aryl and $C_7$–$C_{21}$-aralkyl radicals, or is an acyl or formyl group, by adding a base to a reaction mixture comprising a compound of the general formula (1)

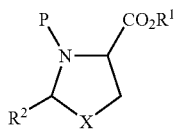

(1)

and an electrophile E-Y where

Y is a leaving group, which comprises carrying out the reaction at a temperature of greater than −40° C.

One possible embodiment of the process according to the invention is carried out diastereoselectively.

The process according to the invention may be applied in a similar manner to all other diastereomers or enantiomers of the reactants of the general formula (1) having the formula (1a), (1b), (1c) or (1d), as long as they are in optically pure form or are a mixture which has at least a uniform configuration at C-2; either only (2R) or only (2S), since this stereogenic center determines the optical induction of the substitution of the electrophile.

For instance, the reactants having the general formulae (1a) and (1b) or their mixtures lead to compounds of the general formula (2a) and reactants having the general formulae (1c) and (1d) or their mixtures to compounds of the general formula (2b).

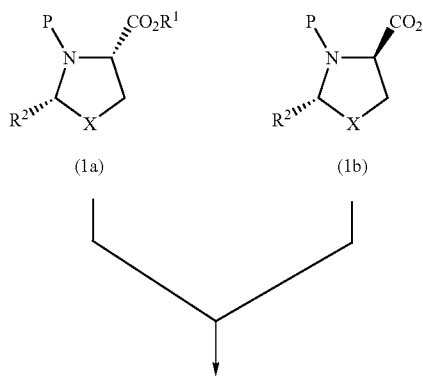

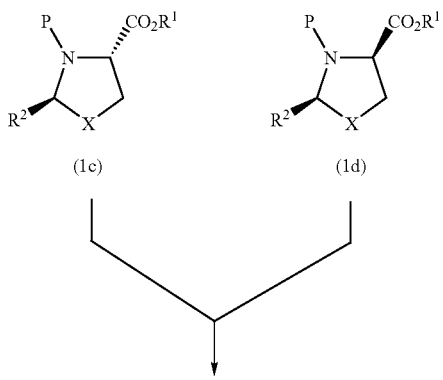

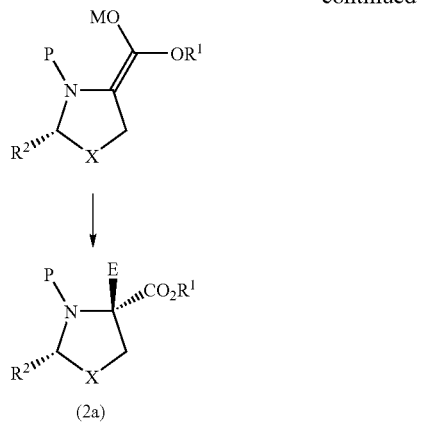

Generally, in the process according to the invention, the reactant of the general formula (1) to be converted or its optically pure forms or their corresponding mixtures are initially charged together with the electrophile, advantageously dissolved in a solvent, and the base is subsequently added.

The addition of the base leads to the formation of a planar, enolate-stabilized anion in the 4-position of the ring and in the α-position to the oxycarbonyl functionality, which is scavenged in situ by the electrophile to form a compound of the general formula (2), and the diastereoselectivity of the reaction is brought about by the intact enantiomerically pure stereogenic center in the 2-position of the ring.

By simple hydrolysis of the resulting compounds of the general formula (2) or of the optical isomers (2a) or (2b), the process according to the invention offers an efficient access route, which can be realized in a simple manner on the industrial scale and is highly diastereoselective and ultimately economically viable, to unnatural, α-substituted amino acids of the general formula (4), in particular their enantiomerically pure forms, for example L-2-methylserine hydrochloride or L-2-methylcysteine hydrochloride.

The process according to the invention can be carried out at distinctly higher temperatures and without the addition of auxiliaries at simultaneously high diastereoselectivity, and thus circumvents the disadvantages known from the prior art which prevented the conversion to an industrial scale process.

In a preferred embodiment of the process according to the invention, optical isomers are obtained in the configuration of the general formula (2a)

by using as reactants optical isomers of the general formulae (1a) or (1b) in pure form or as a mixture

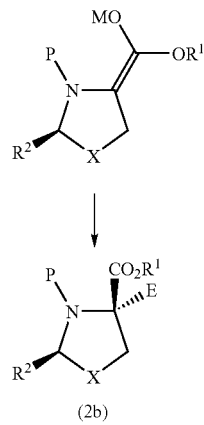

in which the $R^1$, $R^2$, P, E and X radicals are each as defined above, especially selected from the particularly preferred embodiments in each case listed below.

In a particularly preferred embodiment of the process according to the invention, pivalaldehyde ($R^2$=tert-butyl), the methylesters of L-serine or L-cysteine, a formyl protecting group and methyl iodide as the electrophile with lithium hexamethyldisilazide (LiHMN) as the base and final acidic hydrolysis with hydrochloric acid can be used to prepare L-2-methylcysteine hydrochloride and L-2-methylserine hydrochloride respectively in accordance with the following reaction scheme:

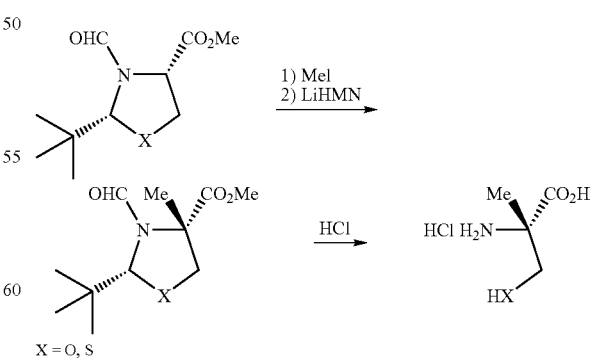

L-2-Methylcysteine and L-2-methylserine which may be obtained from the methylated thiazolidine or oxazolidine (E=Me) by complete hydrolysis may be used directly in further reactions to obtain pharmaceuticals.

The electrophile E-Y to be used for the process according to the invention is generally selected in such a way that it is capable of substituting metal enolates.

The E radical introduced by the electrophile is preferably optionally halogen, cyano, nitro or ester group-functionalized, linear or branched $C_1$–$C_{12}$-alkyl, in particular methyl, ethyl, propyl, butyl, pentyl, hexyl, heptyl, octyl, nonyl or isopropyl, $C_6$–$C_{15}$-aryl, $C_7$–$C_{21}$-aralkyl, in particular benzyl or $C_3$–$C_{10}$-alkenyl, in particular allyl radicals or an acyl or formyl group.

The leaving group Y is preferably selected from the group comprising halogens, tosylates, nitrogen compounds, in particular azides, hydrazides, dialkylamides and sulfonates, in particular chloride, bromide, iodide or alkylsulfonate, most preferably iodide.

A subsequent aqueous hydrolysis then releases the actual reaction products.

The following E radicals may particularly advantageously be introduced by the process according to the invention and are in no way to be interpreted as a restriction:

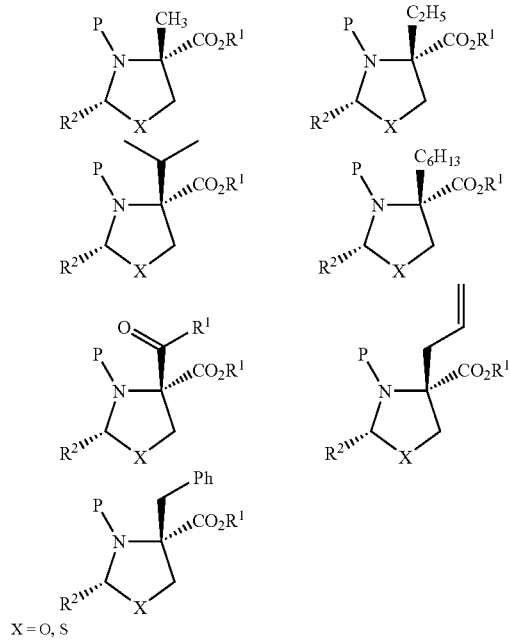

X = O, S

Particularly preferred electrophiles E-Y are methyl iodide, methyl bromide, methyl chloride, methyl tosylate, methyl nonaflate, dimethyl sulfate, in particular dimethyl sulfate and methyl iodide, benzyl iodide, benzyl bromide, benzyl chloride, tolyl bromide, tolyl chloride, ethyl 2-bromoacetate, ethyl 2-iodoacetate, ethyl iodide, ethyl bromide, ethyl triflate, propyl iodide, propyl bromide, isopropyl iodide, isopropyl triflate, hexyl iodide, hexyl triflate, allyl chloride, allyl bromide or allyl iodide, allyl triflate, dimethylformamide and acid chlorides such as acetyl chloride, propanoyl chloride, butanoyl chloride, hexanoyl chloride, octanoyl chloride, pivaloyl chloride, benzoyl chloride, 4-methylbenzoyl chloride.

To protect the amino function against the base used, it is protected in the compounds of the general formula (1) and (2) or their pure optical isomers with an amino protecting group P. Amino protecting group is not restricted thereto, but may be any protecting group which is commonly used to protect amino groups. All common amino protecting groups which are familiar to those skilled in the art from Protecting Groups, P. J. Kocienski, Thieme Verlag, 1994, p. 185–243 may be used for the process according to the invention.

In a preferred embodiment of the process according to the invention, compounds of the general formula (1) which are protected by N-acyl, N-sulfonyl, N-sulfenyl, N-silyl derivatives or N-alkyl groups are used.

Particularly preferred amino protecting groups P are formyl, acetyl, trifluoroacetyl, methoxycarbonyl, ethoxycarbonyl, tert-butoxycarbonyl, benzyloxycarbonyl, allyloxycarbonyl, benzyl, trityl, trialkylsilyl such as trimethylsilyl, triethylsilyl, triisopropylsilyl, tert-butyldimethylsilyl, aryldialkylsilyl such as phenyldimethylsilyl, diarylalkylsilyl such as diphenylmethylsilyl, triarylsilyl such as triphenylsilyl, in particular formyl and acetyl.

The radicals for $R^1$ may be selected from a multitude of possibilities, so that a multitude of substance classes results. They may possibly be organic or silyl esters, the latter especially when nonacidic reaction conditions are initially selected, free acids which then form dianions in the reaction with the base, or mono- or dicarboxylates of the free acid with metals of the first or second main group.

Preferred radicals for $R^1$ which may be used in the process according to the invention are hydrogen, lithium, sodium, potassium, magnesium and calcium.

Further preferred radicals for $R^1$ are from the class of the organic radicals methyl, ethyl, n-propyl, isopropyl, n-butyl, tert-butyl, phenyl or benzyl, and from the class of the silyl radicals trimethylsilyl, triethylsilyl, tributylsilyl, dimethylsilyl, diphenyl, tert-butyldimethylsilyl, thexyldimethylsilyl, norbornyldimethylsilyl, dimethylphenylsilyl, diphenylmethylsilyl, triphenylsilyl.

Diorganosilyl radicals, for example dimethylsilyl and diphenylsilyl, result in compounds of the structure which follows and which can be converted in a similar manner by the process according to the invention and can thus be used as reactants in the sense of compounds of the general formula (2), especially in an optically pure configuration.

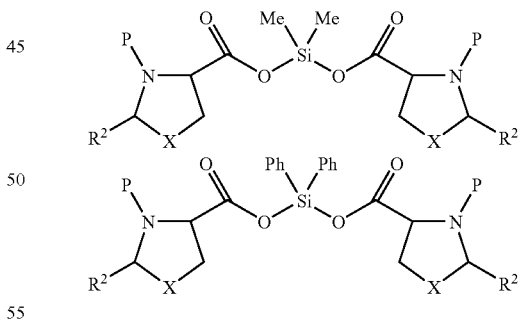

Particularly preferred radicals for $R^1$ are methyl or ethyl.

Particularly preferred radicals for $R^2$ which may be used in the process according to the invention are methyl, ethyl, n-propyl, isopropyl, n-butyl, tert-butyl, cyclohexyl, phenyl, tolyl, naphthyl or benzyl. Particular preference is given to tert-butyl.

The bases used for the process according to the invention may be any which are known to those skilled in the art and can be used to generate a metal enolate.

In a preferred embodiment of the process according to the invention, alkali metal or alkaline earth metal bases, more preferably lithium, sodium and potassium compounds, in particular n-, sec- or tert-butyllithium, potassium tert-butoxide, sodium hydride or tert-butylmagnesium chloride may be used.

In a particularly preferred embodiment of the process according to the invention, nonnucleophilic bases of the general formula (3)

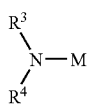
(3)

are used, where $R^3$ and $R^4$ are each independently selected from the group comprising alkyl, aralkyl, aryl and silyl, or $R^3$ and $R^4$ together may also form a cycloalkyl radical in which the $CH_2$ groups of the ring may optionally be substituted by $SiMe_2$ groups or oxygen, and M is selected from the group comprising lithium, sodium, potassium and MgY where Y may in turn be selected from the group comprising chloride, bromide, iodide and a second amide radical $NR^3R^4$.

Particular preference is given to $R^3$ and $R^4$ being trimethylsilyl or isopropyl. Particular preference is given to M being lithium, sodium or potassium.

Especially suitable from the group of the alkali metal amides and alkali metal silazides are lithium, sodium or potassium diisopropylamide, lithium, sodium or potassium hexamethyldisilazide, and lithium, sodium or potassium cyclohexylamide, and from the group of the alkaline earth metal amides and alkaline earth metal silazides, chloromagnesium diisopropylamide, bromomagnesium diisopropylamide, magnesium diisopropylamide, chloromagnesium dicyclohexylamide, chloromagnesium tert-butylamide, chloromagnesium hexamethyldisilazide.

Also particularly suitable for the process according to the invention are alkoxy compounds, in particular magnesium methoxide, magnesium ethoxide, potassium ethoxide, potassium methoxide, sodium ethoxide or sodium methoxide.

For the process according to the invention, the aforementioned bases may be used individually or in the form of mixtures.

Useful solvents for the process according to the invention are all solvents which are inert under the reaction conditions.

Particularly suitable are solvents from the class of the ethers and polyethers, in particular methyl tert-butyl ether, diethyl ether, dipropyl ether, dibutyl ether, tetrahydrofuran, dioxane or 1,2-dimethoxyethane.

The aforementioned solvents may be used alone or as a mixture with other solvents selected from the group comprising aromatic and aliphatic hydrocarbons which are used as a solvent for the base.

Useful solvents are in particular $C_1$–$C_{12}$-alkanes, more preferably pentane, hexane, heptane, octane,-nonane or their branched isomers.

Most preferably suitable for the process according to the invention are tetrahydrofuran or mixtures of tetrahydrofuran with hexane.

In one possible embodiment of the process according to the invention, the reactant of the general formula (1) or its optically pure isomers are dissolved in a suitable solvent and admixed with the electrophile.

From 1 to 10 equivalents, preferably from 1 to 2 equivalents, of the electrophile are used based on the reactant of the general formula (1) or its optically pure isomers.

The temperature, when the electrophile is added and also when the base is subsequently added, is between −40° C. and +100° C., preferably between −30° C. and +30°.

The distinctly higher reaction temperature of the process according to the invention compared to the prior art allows the concentration of the reactants selected to be distinctly higher. In a typical embodiment of the process according to the invention, is is between 0.1 and 5 mol/l, preferably between 0.2 and 1 mol/l.

The addition of the base to the initially charged mixture of the compound of the general formula (1) or its optically pure isomers and the electrophile results in the formation of a metal enolate intermediate which is scavenged in situ by the electrophile.

In the process according to the invention, the amount of base added is from 1 to 5 equivalents based on the compound of the general formula (1) or its optically pure isomers, preferably from 1 to 2 equivalents.

The bases may be used as a solid or dissolved in a solvent. Preference is given to using solutions of the bases in inert solvents, in particular ethers, polyethers, alkanes or aromatics.

Depending on the selected temperature, stirring of the reaction mixture is continued for between 0 min and 4 h, and preference is given to continued reaction times of less than 2 h. An increase in the reaction time does not have any adverse effect on the yield of the desired product.

The compounds of the general formula (2) or their optically pure isomers are worked up and isolated by simple hydrolysis. In general, the reaction mixture is hydrolyzed by adding a protic solvent, in particular water or an alcohol. In one possible embodiment, aqueous solutions of bases, in particular $NH_3$, NaOH, KOH, or acids, in particular HCl, $H_2SO_4$, HOAc, may be used.

The organic phase is subsequently washed to free it of salts and optionally diluted with further organic solvent, and the phases are separated. The organic phase is dried by azeotropic distillation or with a desiccant.

The removal of the solvent leads to the compounds of the general formula (2) or their optically pure isomers which are either further converted directly or optionally further purified by suitable purifying operations such as distillation and recrystallization.

The resulting compounds of the formula (2) or their optically pure isomers, for example (2a), may be converted by literature processes, in particular by hydrochloric acid hydrolysis, to give α-substituted amino acids of the general formula (4) or their optically pure isomers, for example (4a).

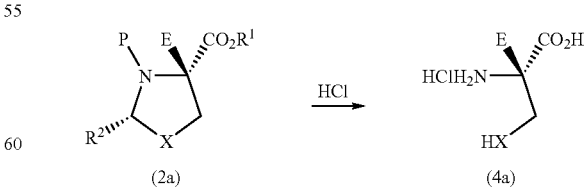

Known processes for preparing compounds of the general formula (4) or their optically pure isomers from compounds of the general formula (2) or their optically pure isomers are known to those skilled in the art from G. Pattenden et al.

(Tetrahedron 1993, 49(10), 2131–2138), G. Mulqueen et al. (Tetrahedron 1993, 49(24), 5359–5364) or from WO 01/72702.

In general, the compounds of the general formula (2) or their optically pure isomers are dissolved to approx. 0.3 mol/l in 5M HCl and heated to reflux. This cleaves the heterocycle and generally detaches the protecting group and also the ester function. When acid-resistant protecting groups P and/or $R^1$ are used, it is necessary in an additional step to detach these protecting groups by proceeding in a suitable manner known from the literature, in particular as described for amino protecting groups P in Protecting Groups, P. J. Kocienski, Thieme Verlag, 1994, 185–243, and ester functions $R^1$ in Protecting Groups, P. J. Kocienski, Thieme Verlag, 1994, 118–154.

DETAILED DESCRIPTION OF THE PREFERRED EMBODIMENTS

The examples which follow serve to illustrate the invention in detail and are in no way to be interpreted as a restriction.

EXAMPLE

Example 1

Methyl (2R,4R)-2-tert-butyl-3-formyl-1,3-thiazolidine-4-allyl-4-carboxylate

A laboratory reactor was initially charged with methyl (2R,4R)-2-tert-butyl-3-formyl-1,3-thiazolidine-4-carboxylate (20.8 g) which was dissolved in anhydrous THF (100 ml) and cooled to −25° C. Allyl bromide (8.5 ml) was metered in. Subsequently, lithium hexamethyldisilazide solution (100 ml, 1M in THF) was slowly added dropwise. The reaction mixture was quenched using 15% acetic acid, the phases were separated and the organic phase was concentrated by evaporation, taken up in MTBE, washed with $H_2O$ and concentrated by evaporation again. Yield 23.2 g of brownish oil (95%), methyl (2R,4R)-2-tert-butyl-3-formyl-1,3-thiazolidine-4-allyl-4-carboxylate.

HPLC content of crude product: reactant <0.5%, product 92.6%, two nonidentified peaks at 1.5 and 4.5%. NMR ($CDCl_3$, 300 MHz): conformer ratio 53:47; 0.94 and 1.06 (9 H, s, $C(CH_3)_3$), 2.80–3.12 (3 H, m, $CH_2CHCH_2$ and $CH_2S$), 3.28 and 3.70 (1 H, d, $CH_2S$), 3.78 and 3.82 (3 H, s, $CO_2CH_3$), 4.65 and 5.37 (1 H, s, $CHC(CH_3)_3$), 5.05–5.25 (2 H, m, $CH_2CHCH_2$), 5.70–5.85 and 5.95–6.12 (2 H, m, $CH_2CHCH_2$), 8.35 and 8.52 (1 H, s, CHO).

Example 2

Methyl (2R,4R)-2-tert-butyl-3-formyl-1,3-thiazolidine-4-benzyl-4-carboxylate

A laboratory reactor was initially charged with methyl (2R,4R)-2-tert-butyl-3-formyl-1,3-thiazolidine-4-carboxylate (40 g) which was dissolved in anhydrous THF (200 ml) and cooled to −25° C. Benzyl bromide (22.7 ml) was added. The lithium hexamethyldisilazide solution (190 ml, 1M in THF) was slowly metered in. After the end of the reaction, the reaction mixture was quenched with 15% acetic acid, the phases were separated and the organic phase was concentrated by evaporation, taken up in MTBE, washed with $H_2O$ and concentrated by evaporation again. The resulting oil slowly crystallized through and was triturated with petroleum ether. Yield 42.0 g of orange solid (77%), methyl (2R,4R)-2-tert-butyl-3-formyl-1,3-thiazolidine-4-benzyl-4-carboxylate.

HPLC content of crude product: product 96.2%, reactant undetectable, benzyl bromide 0.8%. After recrystallization from petroleum ether/ethyl acetate: colorless crystals, purity >99.5%. NMR ($CDCl_3$, 300 MHz): conformer ratio 60:40; 0.94 and 1.03 (9 H, s, $C(CH_3)_3$), 2.95–3.65 (4 H, m, 2 x $CH_2$), 3.76 and 3.78 (3 H, s, $CO_2CH_3$), 4.50 and 5.36 (1 H, s, $CHC(CH_3)_3$), 7.05–7.14 (1 H, m, ArH), 7.20–7.36 (4 H, m, ArH), 8.45 and 8.67 (1 H, s, CHO).

Example 3

Methyl (2R,4R)-2-tert-butyl-3-formyl-1,3-thiazolidine-4-benzoyl-4-carboxylate

A laboratory reactor was initially charged with methyl (2R,4R)-2-tert-butyl-3-formyl-1,3-thiazolidine-4-carboxylate (20.8 g), dissolved in anhydrous THF (100 ml) and cooled to −25° C. Benzoyl chloride (11.6 ml) was metered in. The lithium hexamethyldisilazide solution (100 ml, 1M in THF) was then metered in slowly. The reaction mixture was quenched with 15% acetic acid, the phases were separated, and the organic phase was concentrated by evaporation, taken up again in MTBE, washed with $H_2O$ and concentrated by evaporation again. Yield 34.5 g of brown oil (quantitative, still contained acetic acid residues), methyl (2R,4R)-2-tert-butyl-3-formyl-1,3-thiazolidine-4-benzoyl-4-carboxylate.

HPLC content of crude product: reactant undetectable, product 82.8%, remainder several unidentified relatively small peaks.

After chromatographic purification: 97.8%.

NMR ($CDCl_3$, 300 MHz): conformer ratio 79:21; 1.00 and 1.06 (9 H, s, $C(CH_3)_3$), 3.41 (1 H, d, $CH_2$), 4.36 (1 H, d, $CH_2$), 3.80 and 3.83 (3 H, s, $CO_2CH_3$), 4.95 and 5.54 (1 H, s, $CHC(CH_3)_3$), 7.35–7.65 (3 H, m, ArH), 7.90–8.05 (4 H, m, ArH), 8.30 and 8.43 (1 H, s, CHO).

Example 4

Methyl (2R,4R)-2-tert-butyl-3-formyl-1,3-thiazolidine-4-ethyl-4-carboxylate

A laboratory reactor was initially charged with methyl (2R,4R)-2-tert-butyl-3-formyl-1,3-thiazolidine-4-carboxylate (37.5 g) which was dissolved in anhydrous THF (180 ml) and cooled to −25° C. Ethyl trifluoromethanesulfonate (23 ml) was metered in. The lithium hexamethyldisilazide solution (180 ml, 1M in THF) was then slowly metered in. The reaction mixture was quenched using 15% acetic acid and diluted with sat. NaCl solution, the phases were separated, and the organic phase was concentrated by evaporation, taken up in MTBE, washed with $H_2O$ and concentrated under reduced pressure. Yield 43.5 g of orange oil (quantitative, still contained acetic acid), methyl (2R,4R)-2-tert-butyl-3-formyl-1,3-thiazolidine-4-ethyl-4-carboxylate.

HPLC content of crude product: 2.1% of reactant, 94.3% of product, two further peaks (1.2%, 2.2%) unidentifiable. NMR ($CDCl_3$, 300 MHz): conformer ratio 76:24; 0.95 and 1.05 (9 H, s, $C(CH_3)_3$), 1.01 (3 H, t, $CH_2CH_3$), 2.12 (2 H, m, $CH_2CH_3$), 3.00 and 3.35 (1 H, d, $CH_2$), 3.73 (1 H, d, $CH_2$), 3.78 and 3.81 (3 H, s, $CO_2CH_3$), 4.72 and 5.42 (1 H, s, $CHC(CH_3)_3$), 8.40 and 8.47 (1 H, s, CHO).

Example 5

Methyl (2R,4R)-2-tert-butyl-3-formyl-1,3-thiazolidine-4-methyl-4-carboxylate n-BuLi (1.6M in hexane, 100 ml) was initially charged and 1,1,3,3-hexamethyldisilazane (35.5 ml) was added dropwise with ice cooling. The solution was warmed to RT. A second flask was initially charged with methyl (2R,4R)-2-tert-butyl-3-formyl-1,3-thiazolidine-4-carboxylate (31.9 g) which was dissolved in anhydrous THF (190 ml) gelöst and cooled to −280C. Methyl iodide (10.0 ml) was metered in. The lithium hexamethyldisilazide solution was then metered in and the progress of the reaction was followed by GC. On completion of conversion, the reaction mixture was quenched with dilute acetic acid, the phases were separated and the organic phase was concentrated by evaporation, taken up in MTBE and washed with water, and concentrated under reduced pressure. Yield 31.1 g (92%), methyl (2R,4R)-2-tert-butyl-3-formyl-1,3-thiazolidine-4-methyl-4-carboxylate.

GC content of crude product: 0.3% of reactant, 97.1% of product, 1,7% of N-formyl-N-(2-methylthio-3,3-dimethyl-1-propyl)dehydroalanine methyl ester.

NMR ($CDCl_3$, 300 MHz): conformer ratio 70:30; 0.96 and 1.07 (9 H, s, $C(CH_3)_3$), 1.67 and 1.70 (3 H, s, $CH_3$), 2.72 and 2.86 (1 H, m, $CH_2$), 3.32 and 3.65 (1 H, d, $CH_2$), 3.76 and 3.83 (3 H, s, $CO_2CH_3$), 4.66 and 5.30 (1 H, s, C$\underline{H}C(CH_3)_3$), 8.29 and 8.42 (1 H, s, CHO).

Example 6

L-2-Methylcysteine hydrochloride

5M HCl (175 ml) was poured over a portion of the product (15 g) and boiled to reflux for 3 d. Afterwards, the hydrochloric acid was distilled off and the product was concentrated to dryness by evaporation, and crystallization was induced by scratching. L-2-Methylcysteine, beige powder (9.7 g, 92%). A portion was derivatized with formaldehyde for ee determination and analyzed by HPLC (Chirobiotic T, 250×4.6 mm, Astec): 99.3% ee.

Example 7

Methyl (2R,4S)-2-tert-butyl-3-formyl-1,3-oxazolidine-4-methyl-4-carboxylate

A laboratory reactor was initially charged with methyl (2R,4S)-2-tert-butyl-3-formyl-1,3-oxazolidine-4-carboxylate (19.4 g) which was dissolved in anhydrous THF (100 ml) and cooled to −25° C. Methyl iodide (6.2 ml) was metered in. The lithium hexamethyldisilazide solution (100 ml, 1M in THF) was then metered in slowly. After heating, the reaction mixture was quenched with 15% acetic acid and diluted with sat. NaCl solution, the phases were separated and the organic phase was concentrated by evaporation, taken up in MTBE and washed with $H_2O$. The combined organic phases were reextracted once with MTBE and all organic phases were concentrated under reduced pressure. Yield 16.1 g (78%) of methyl (2R,4S)-2-tert-butyl-3-formyl-1,3-oxazolidine-4-methyl-4-carboxylate. GC content of crude product: 1.8%, 5.3%, 1.7% (three unidentified secondary products), 82.7% of product, 3.8% of unidentified secondary product.

The yield of isolated crude product (78%) and its content (82.7%) result in a theoretical yield of 65% of pure product.

NMR ($CDCl_3$, 300 MHz): conformer ratio 54:46; 0.92 and 1.02 (9 H, s, $C(CH_3)_3$), 1.68 and 1.69 (3 H, s, $CH_3$), 3.60–3.80 (1 H, m, $CH_2$), 4.30 and 4.68 (1 H, d, $CH_2$), 3.75 and 3.78 (3 H, s, $CO_2CH_3$), 4.93 and 5.28 (1 H, s, C$\underline{H}C(CH_3)_3$), 8.37 and 8.49 (1 H, s, CHO).

Example 8

Methyl (2R,4R)-2-tert-butyl-3-formyl-1,3-thiazolidine-4-methyl-4-carboxylate

A laboratory reactor was initially charged with methyl (2R,4R)-2-tert-butyl-3-formyl-1,3-thiazolidine-4-carboxylate (20.8 g) which was dissolved in anhydrous THF (130 ml) and cooled to −25° C. Methyl iodide (6.2 ml dissolved in 20 ml THF) was added. A solution of potassium-tert-butoxide (11.2 g) in THF (50 ml) was slowly metered in. The reaction progress at −25° C was monitored by GC. The reaction mixture was warmed up to room temperature after 4h. The reaction mixture was quenched with 6% ammonia solution. Methyl-tert-butylether (MTBE) was added and the resulting two phases separated. The organic layer was concentrated by evaporation. The residue was taken up in MTBE and washed with 1M HCl. The clear organic layer was evaporated in vacuo. Crude yield 16.7 g. The $^1$H-NMR spectrum showed that the desired compound was the major product of the reaction along with some decomposition products which have not been identified. Content of crude product: 79.0 GC-Area %.

Example 9

Methyl (2R,4R)-2-tert-butyl-3-formyl-1,3-thiazolidine-4-methyl-4-carboxylate

A laboratory reactor was initially charged with methyl (2R,4R)-2-tert-butyl-3-formyl-1,3-thiazolidine-4-carboxylate (20.8 g) which was dissolved in anhydrous THF (130 ml) and cooled to −25° C. Methyl iodide (6.2 ml dissolved in 20 ml THF) was added. A solution of sodium hexamethyldisilazide (49.8 ml as 40% solution in THF) dissolved in THF (50 ml) was slowly metered in. The reaction progress at −25° C. was monitored by GC. After 3 h the reaction mixture was warmed to room temperature and quenched mit 15% acetic acid (140 ml). Phases were separated, the organic layer washed once with aqueous ammonia solution (12.5%; 120 ml) and evaporated in vacuo. Crude yield 20.3 g. Purity (GC) 85.7 Area % methyl (2R,4R)-2-tert-butyl-3-formyl-1,3-thiazolidine-4-methyl-4-carboxylate, 10.7% methyl N-formyl-N-(1-methylthio-2,2-dimethyl-1-propyl)-dehydroalaninate, all other peaks <1 Area %.

Example 10

Methyl (2R,4R)-2-tert-butyl-3-formyl-1,3-thiazolidine-4-methyl-4-carboxylate

A laboratory reactor was initially charged with methyl (2R,4R)-2-tert-butyl-3-formyl-1,3-thiazolidine-4-carboxylate (20.5 g) which was dissolved in anhydrous THF (100 ml) and cooled to −25° C. Methyl trifluoromethanesulfonate (11.0 ml) was added. Lithium hexamethyldisilazide solution (100 ml, 1M in THF) was slowly metered in. The reaction mixture was quenched with 15% acetic acid, diluted with brine, phases separated and the organic phase was concentrated by evaporation, taken up in MTBE, washed with $H_2O$ and concentrated by evaporation again. Yield 21.8 g, yellow oil (99%, still contains traces of acetic acid), methyl (2R,4R)-2-tert-butyl-3-formyl-1,3-thiazolidine-4-methyl-4-carboxylate. HPLC content of crude product: >95%. $^1$H-NMR in accordance with example 5.

Example 11

Methyl (2R,4R)-2-tert-butyl-3-formyl-1,3-thiazolidine-4-methyl-4-carboxylate A flask was charged with methyl (2R,4R)-2-tert-butyl-3-formyl-1,3-thiazolidine-4-carboxylate (9.95 g) which was dissolved in anhydrous THF (60 ml) and cooled by an ice-water bath to +5° C. Methyl iodide (3.15 ml) dissolved in THF (9 ml) was added. Lithium hexamethyldisilazide solution (prepared from 1.6M butyl lithium in hexane (31.2 ml) hexamethyldisilazane (11.1 ml)) was added dropwise, keeping the temperature below +25° C. The reaction mixture was quenched with 15% acetic acid and diluted with ethyl acetate. Layers were separated, the organic layer was washed with diluted ammonia (12.5%; 100 ml) and concentrated in vacuo. Yield 10.8 g orange to brownish oil (contains some acetic acid and residual silyl compounds). The $^1$H-NMR spectrum of the major product is in accordance with example 5. Content of pure compound is 69.9 weight % (by calibrated HPLC, external standard).

Accordingly, while only a few embodiments of the present invention have been shown and described, it is obvious that many changes and modifications may be made thereunto without departing from the spirit and scope of the invention.

What is claimed is:

1. A process for preparing compounds of the general formula (2)

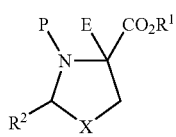
(2)

where

X is S or O and $R^1$ is selected from the group consisting of hydrogen, metals of the first or second main group, linear or branched $C_1$–$C_{12}$-alkyl, $C_6$–$C_{15}$-aryl or $C_7$–$C_{21}$-aralkyl radicals, dialkylsilyl and trialkylsilyl, dialkylarylsilyl, diarylalkylsilyl, triarylsilyl radicals, and the organic radicals of the silyl radicals are in turn selected from $C_1$–$C_{12}$-alkyl and $C_6$–$C_{15}$-aryl radicals and $R^2$ is selected from the group consisting of linear or branched $C_1$–$C_{12}$-alkyl, $C_6$–$C_{15}$-aryl and $C_7$–$C_{21}$-aralkyl radicals and P is an amino protecting group and E is a radical selected from the group consisting of optionally halogen, cyano, nitro or ester group-substituted, linear or branched $C_1$–$C_{12}$-alkyl, $C_3$–$C_{10}$-alkenyl, $C_6$–$C_{15}$-aryl and $C_7$–$C_{21}$-aralkyl radicals, or is an acyl or formyl group, comprising adding a base to a reaction mixture comprising a compound of the general formula (1)

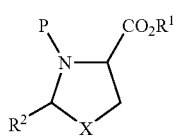
(1)

and an electrophile E-Y where

Y is a leaving group, and carrying out the reaction at a temperature of greater than −40° C.

2. A process for preparing optical isomers in the configuration of the general formula (2a)

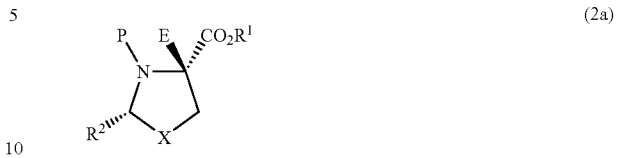
(2a)

using optical isomers of the general formulae (1a) or (1b) in pure form or as mixtures

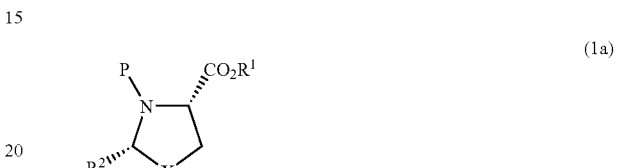
(1a)

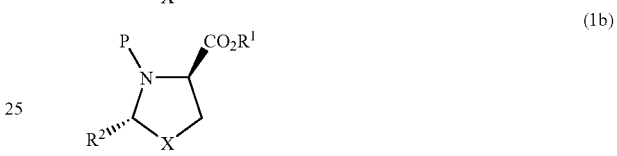
(1b)

where

X is S or O and $R^1$ is selected from the group consisting of hydrogen, metals of the first or second main group, linear or branched $C_1$–$C_{12}$-alkyl, $C_6$–$C_{15}$-aryl or $C_7$–$C_{21}$-aralkyl radicals, dialkylsilyl and trialkylsilyl, dialkylarylsilyl, diarylalkylsilyl, triarylsilyl radicals, and the organic radicals of the silyl radicals are in turn selected from $C_1$–$C_{12}$-alkyl and $C_6$–$C_{15}$-aryl radicals and $R_2$ is selected from the group comprising linear or branched $C_1$–$C_{12}$-alkyl, $C_6$–$C_{15}$-aryl and $C_7$–$C_{21}$-aralkyl radicals and P is an amino protecting group and E is a radical selected from the group consisting of optionally halogen, cyano, nitro or ester groupsubstituted, linear or branched $C_1$–$C_{12}$-alkyl, $C_3$–$C_{10}$-alkenyl, $C_6$–$C_{15}$-aryl and $C_7$–$C_{21}$-aralkyl radicals, or is an acyl or formyl group, comprising adding a base to a reaction mixture comprising a compound of the general formula (1)

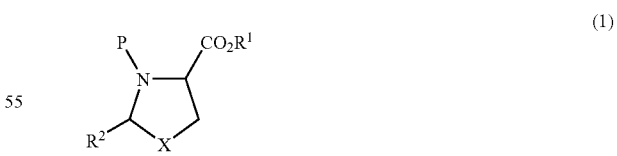
(1)

and an electrophile E-Y where

Y is a leaving group, and carrying out the reaction at a temperature of greater than −40° C.

3. The process of claim 1, wherein P is selected from the group consisting of alkyl, formyl, acyl, oxycarbonyl, sulfonyl, sulfenyl and silyl radicals.

4. The process of claim 1, wherein Y is selected from the group consisting of halogens, tosylates, azides, hydrazides, dialkylamides and sulfonates.

5. The process of claim 1, wherein the base is an alkali metal amide.

6. The process of claim 1, wherein E-Y is methyl iodide or dimethyl sulfate.

7. The process of claim 1, wherein the process is carried out at a temperature of from −30° C. to +30° C.

8. The process of claim 1, wherein $R^1$ is selected from the group consisting of hydrogen, methyl, ethyl, n-propyl, isopropyl, n-butyl, tert-butyl, phenyl, benzyl, trimethylsilyl, triethylsilyl and tributylsilyl.

9. The process of claim 1, wherein $R^2$ is selected from the group consisting of methyl, ethyl, n-propyl, isopropyl, n-butyl, tert-butyl, cyclohexyl, phenyl, tolyl, naphthyl and benzyl.

10. The process of claim 2, wherein P is selected from the group consisting of alkyl, formyl, acyl, oxycarbonyl, sulfonyl, sulfenyl and silyl radicals.

11. The process of claim 2, wherein Y is selected from the group consisting of halogens, tosylates, azides, hydrazides, dialkylamides and sulfonates.

12. The process of claim 2, wherein the base is an alkali metal amide.

13. The process of claim 2, wherein E-Y is methyl iodide or dimethyl sulfate.

14. The process of claim 2, wherein the process is carried out at a temperature of from −30° C. to +30° C.

15. The process of claim 2, wherein $R^1$ is selected from the group consisting of hydrogen, methyl, ethyl, n-propyl, isopropyl, nbutyl, tert-butyl, phenyl, benzyl, trimethylsilyl, triethylsilyl and tributylsilyl.

16. The process of claim 2, wherein $R^2$ is selected from the group consisting of methyl, ethyl, n-propyl, isopropyl, n-butyl, tert-butyl, cyclohexyl, phenyl, tolyl, naphthyl and benzyl.

* * * * *